(12) United States Patent
Alekseyenko et al.

(10) Patent No.: US 8,075,470 B2
(45) Date of Patent: Dec. 13, 2011

(54) THERAPEUTIC DEVICE FOR LOCAL AREA STIMULATION

(76) Inventors: Nikolay Alekseyenko, Pacifica, CA (US); John Frederick Decker, San Francisco, CA (US)

( * ) Notice: Subject to any disclaimer, the term of this patent is extended or adjusted under 35 U.S.C. 154(b) by 853 days.

(21) Appl. No.: 12/150,823

(22) Filed: Apr. 30, 2008

(65) Prior Publication Data

US 2008/0207984 A1    Aug. 28, 2008

Related U.S. Application Data

(63) Continuation of application No. 11/124,721, filed on May 7, 2005, now abandoned, which is a continuation-in-part of application No. 11/002,781, filed on Dec. 2, 2004, now abandoned.

(51) Int. Cl.
   *A61N 1/00*    (2006.01)
(52) U.S. Cl. ........................................................ 600/13
(58) Field of Classification Search ................ 600/9–15; 606/32–33, 41–42
   See application file for complete search history.

(56) References Cited

U.S. PATENT DOCUMENTS

| | | | | |
|---|---|---|---|---|
| 6,338,347 | B1 * | 1/2002 | Chung | 600/9 |
| 2005/0011030 | A1 * | 1/2005 | Gonzalez | 15/160 |

* cited by examiner

*Primary Examiner* — John Lacyk
(74) *Attorney, Agent, or Firm* — Schneck & Schneck

(57) ABSTRACT

A therapeutic device and process utilizes an array of members in which each member is both magnetically coupled to a magnetic source and electrically coupled to a source of electrical signals. In the preferred embodiment, the members include both ferromagnetic members and diamagnetic members. The members are controlled to enable variations of electromagnetic stimuli by selectively adjusting applied electrical signals to the two types of members. The ferromagnetic members and the diamagnetic members may be placed in alternating rows. The rows may be individually controlled with respect to applying alternative electrical signals, as well as with respect to enablement and disablement. A thermal module may be included in order to also apply thermal stimulus. Some embodiments include the capability to monitor effects of the stimuli to the skin of the person.

16 Claims, 23 Drawing Sheets

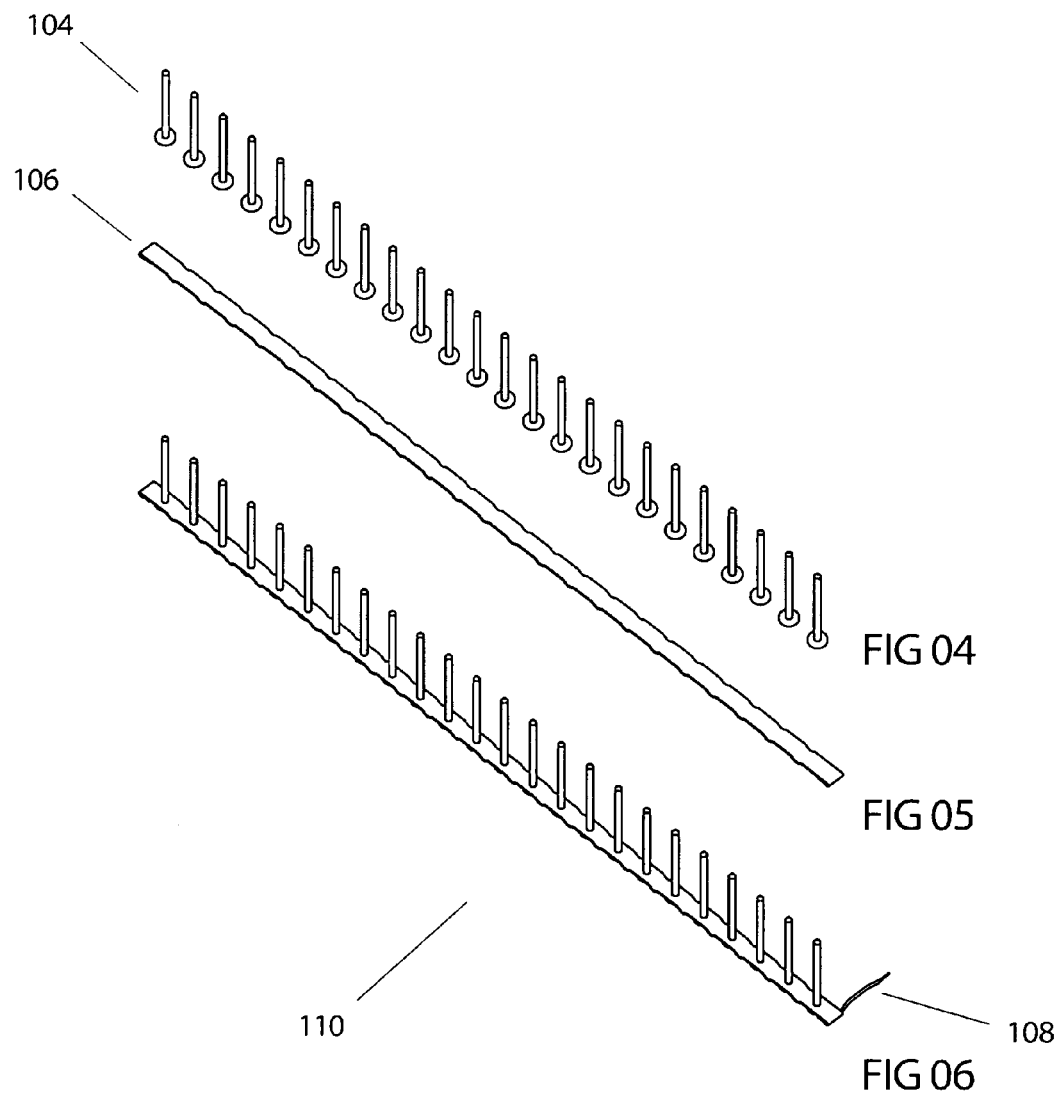

THERAPEUTIC DEVICE FOR LOCAL AREA STIMULATION

CROSS REFERENCE TO RELATED APPLICATIONS

This application is a continuation of U.S. patent application Ser. No. 11/124,721, filed on May 7, 2005 now abandoned, which is a continuation in part of U.S. patent application Ser. No. 11/002,781, filed on Dec. 2, 2004, now abandoned, which is incorporated by reference in its entirety herein.

BACKGROUND ART

This invention pertains to the field of processes and devices used by healing arts and medical practitioners to stimulate healing responses and promote health in their subjects as well as the field of processes and devices used to investigate bio-electromagnetic phenomena.

Healing arts practitioners in a wide variety of disciplines and traditions have long observed the therapeutic value of a variety of local stimuli. From hot water bottles to acupuncture needles, from electrical currents to magnetic fields, and from massages to plasters, many stimuli are recognized as helpful components in therapy. They are administered continuously or intermittently, constant or modulated, over a wide range of intensities from extremely fine to much higher, and, in the case of electrical and magnetic stimuli, with constant or alternating polarities.

Fields of practice using such stimuli include the now-standard practice of promoting the healing of bone fractures by inducing strong electromagnetic fields, sports and rehabilitative medicine, physical therapy, acupuncture, acupressure, therapeutic massage, and less traditional practices such as magneto-therapy and "biofeedback" therapy.

A number of devices have been invented to aid in administering therapeutic stimuli. Following are descriptions of four such devices cited as examples of prior art.

A device for intramuscular stimulation therapy by application of local electric currents is described in U.S. Pat. No. 6,058,938 to Chu et al. (1998). The device has an electric battery power source connected to conductive tips held on Teflon (a registered trademark of E.I. DuPont de Nemours and Company) handles and inserted subcutaneously. One concern is that use of the device is necessarily intrusive, since it requires insertion of the tips.

A related device is identified in U.S. Pat. No. 4,590,936 to Sakowski (1984). This device is used to reduce pain according to acupressure principles through application of local mechanical pressure. Shortcomings of this device are that its use precludes simultaneous administration of other stimuli singly or in combination.

A third device is proposed in U.S. Pat. No. 4,319,574 to Sun et al. (1980). It also applies physical pressure and is used to stimulate "Biologically Active Spots" (BAS). It consists of a flat plate with two protruding parts that move against each other by means of an electromagnet. The parts have adjustable positions set by selectable stops. Similar to the Sakowski device, this device may provide therapeutic benefits, but is limited because it neither provides nor permits simultaneous application of other stimuli singly or in combination. Additionally, this device requires an external electrical power supply.

The three above-described devices are limited to administration of one type of stimulus and make simultaneous administration of other stimuli impractical. They are localized to one point or, in the case of the first device, a line between two points.

A fourth device is actually a range of devices based on a common fundamental feature. Inventor and healing practitioner Igor Kuznetsov developed his "IPLIKATOR" in Russia. Kuznetsov's writings and marketing materials cite ancient traditions such as India's fakir's lying on beds of nails or walking on beds of burning coals and Chinese acupuncture as precedents for his invention. All versions of his device employ points (thermoplastic) spaced 1cm or more apart or, uncommonly, needles (metal) spaced at least 8mm apart. A variation of IPLIKATOR dubbed "Panacea" has been offered for sale in North America and is comprised of a pad with integral molded parts, similarly spaced.

Kuznetsov's device, in the form sold over the counter in Russia until the collapse of the Soviet Union, has molded plastic points spaced approximately 1 cm apart. A version with metal needles set 8 mm apart was used in clinical settings. Kuznetsov's instructions for using his device reflect the fundamental difference between it and the present invention. Kuznetsov's instructions for use reveal a singular feature of his device: it relies on physical pressure being applied at maximum tolerable pain levels, followed by release of the pressure for relief followed by a repeat application of maximum tolerable pressure and so on until the desired response is noted or, in cases of local application, the underlying musculature becomes entirely limp and "the points press against bone." Following proper application, a subject's skin, though not lacerated, is characteristically marked by epidermal abrasions where the points have pressed and surrounded by "stretch marks" indicating acute distension of the skin radiating out from the points. The device works through mechanical distension of skin and underlying tissue in a species of massage and by inducing intense pain. Both aspects depend on mechanical pressure being applied to points that are spaced far enough apart to significantly deform the skin surface.

Kuznetsov and his followers cite the mechanical deformation and the pain as intrinsic to the use of the device and its effects. They conjecture in addition that pushing hundreds or thousands of spots will inevitably hit a few "acupuncture points" as well, with therapeutic benefit.

The potential benefits of the Kuznetsov devices are not universally recognized. Regardless, it is well recognized that further advances in the therapeutic field are always desirable.

SUMMARY OF THE INVENTION

In accordance with one preferred embodiment of the present invention, a therapeutic device for applying local area stimuli includes an array of metal points set approximately 3mm to 6mm apart, arranged in rows alternating between ferromagnetic and diamagnetic materials, and held in a flexible, magnetized support, the combined parts so connected and deployed as to effectively administer and monitor a wide variety of physical stimuli singly or in combination. The device may also be used as a tool to provide a means to effectively monitor coincident and concurrent biophysical responses to these stimuli for therapeutic purposes or scientific research.

Accordingly, the therapeutic device uses points in an array to provide gentle and non-invasive therapeutic stimuli across a surface area of a person's body. In operation, the device applies galvanically fine degrees of electrical potential or current and electromagnetic fields. At least in the preferred embodiment, there is no requirement for an external power source. Preferably, the points are arranged to apply stimuli evenly over an area of application while varying the stimuli at smaller scales. The use of both ferromagnetic points and diamagnetic points, as in the preferred embodiment, provides variations of the stimuli at the smaller scales, but this can be additionally or alternatively provided by the arrangement of the points and/or the interconnections of the points. The stimuli may be applied in differing degrees or kinds with respect to selectable subportions of the area of application to the person. The stimuli may be either or both of electrical and magnetic stimuli. In some embodiments, heat or cold is applied to the area of application.

As previously noted, the device may be used to monitor physical changes. The monitored property may include field polarities, magnetic moment, or electrical resistance at selected areas of application during a course of treatment. It is also possible to accommodate simultaneous topical or subcutaneous administration of medicinal substances and/or additional highly localized stimuli. Thus, the device may be used to activate or enhance medicinal substances by means of electrical, magnetic and/or thermal fields.

The therapeutic device may be modular. The various functions may be provided by separate components or modules which operate alone or in combination. Where the components and modules are replaceable, a wide variety of sources of stimuli and controllers of the stimuli may be implemented, as well as the possibility of providing concurrent monitoring of the stimuli, their biophysical effects, and the biophysical conditions or responses within the device's domain of influence.

BRIEF DESCRIPTION OF THE DRAWINGS

FIG. 04 is a perspective view of a point row.

FIG. 05 is a perspective view of a conductive strip.

FIG. 06 is a perspective view of the point row of FIG. 04 and the conductive strip of FIG. 05 assembled into a point row assembly with a conductive wire attached.

DETAILED DESCRIPTION

Figure 1:
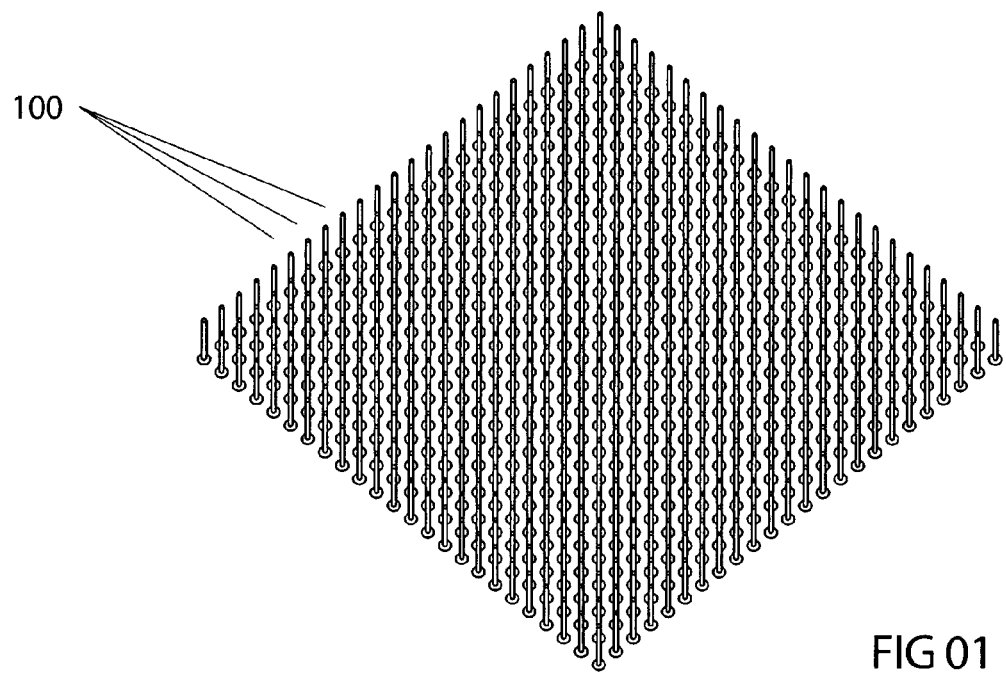
FIG. 01 is a perspective view of an array of points in accordance with the invention.
Figure 2:
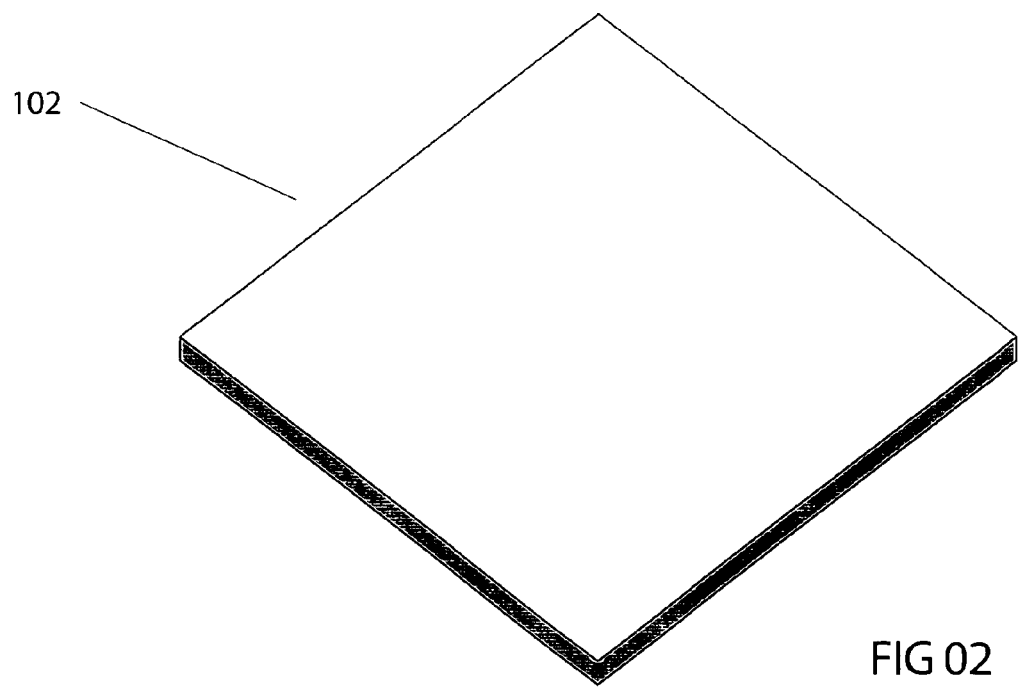
FIG. 02 is a perspective view of a flexible base block in accordance with the invention.
Figure 3:
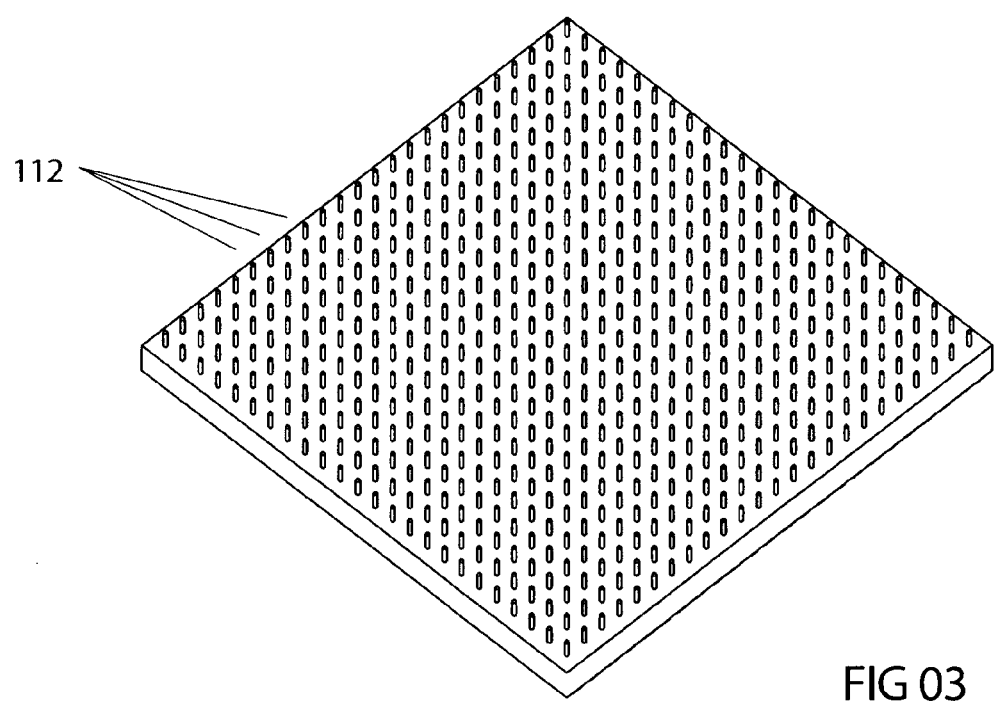
FIG. 03 is a perspective view of the point array of FIG. 01 embedded in the flexible base block of FIG. 02.

With reference to FIGS. 01-03, the invention 112 includes an array of points 100 supported so as to be assembled together with some or all of the points regularly spaced approximately 3 mm to 6 mm apart. This point array is used to provide a physical stimulus at the skin surface to the subject under treatment. It has been observed that this arrangement is unexpectedly able to induce useful responses not seen in other forms of stimulation that have been used to induce and support healing.

The galvanic effects described below are particularly dependent on the points not being set too far apart. The modulation of magneto-electrical fields is seen to be therapeutically effective in the spacing specified. It is hypothesized that this spacing reflects underlying granularity of the vascular and nervous systems, i.e., the first level of organization of capillaries and nerve endings. It is further hypothesized that the variations of stimuli at this scale are related in magnitude to the scale of biochemical and bioelectrical processes in living tissues. Finally, it is hypothesized that this scale is consonant with the thickness of dermal layers, the skin, sometimes referred to as "the body's largest organ."

By using a flexible support 102 in a planar-like array, the points 100 can be quite sharp and yet not break the subject's skin because skin is elastic and properly supported point arrays, flexing under subject pressure, distribute the pressure evenly. The gentle, non-injurious irritation by these points, at least some of which are set apart as specified, affects dermal structures which have granularity at magnitudes of scale similar to the point spacings and to the depth of electromagnetic field deformations induced through the points.

This effect of scale is most evident with the use of metal points 100 so connected as to permit application of electrical current or potential, enhancing therapeutic benefits in an unexpected manner and degree, therapeutic effects comparable to electro-acupuncture in their immediacy, intensity and benefit, even though they are not to be confused with acupuncture itself.

The flexible support 102 of FIGS. 02 and 03 is a synthetic, rubbery "magnetophore" material which is permanently magnetized by added ferromagnetic ingredients, similar to refrigerator magnets. This provides benefits of a magnetic field as a therapeutic stimulus.

Figure 9:
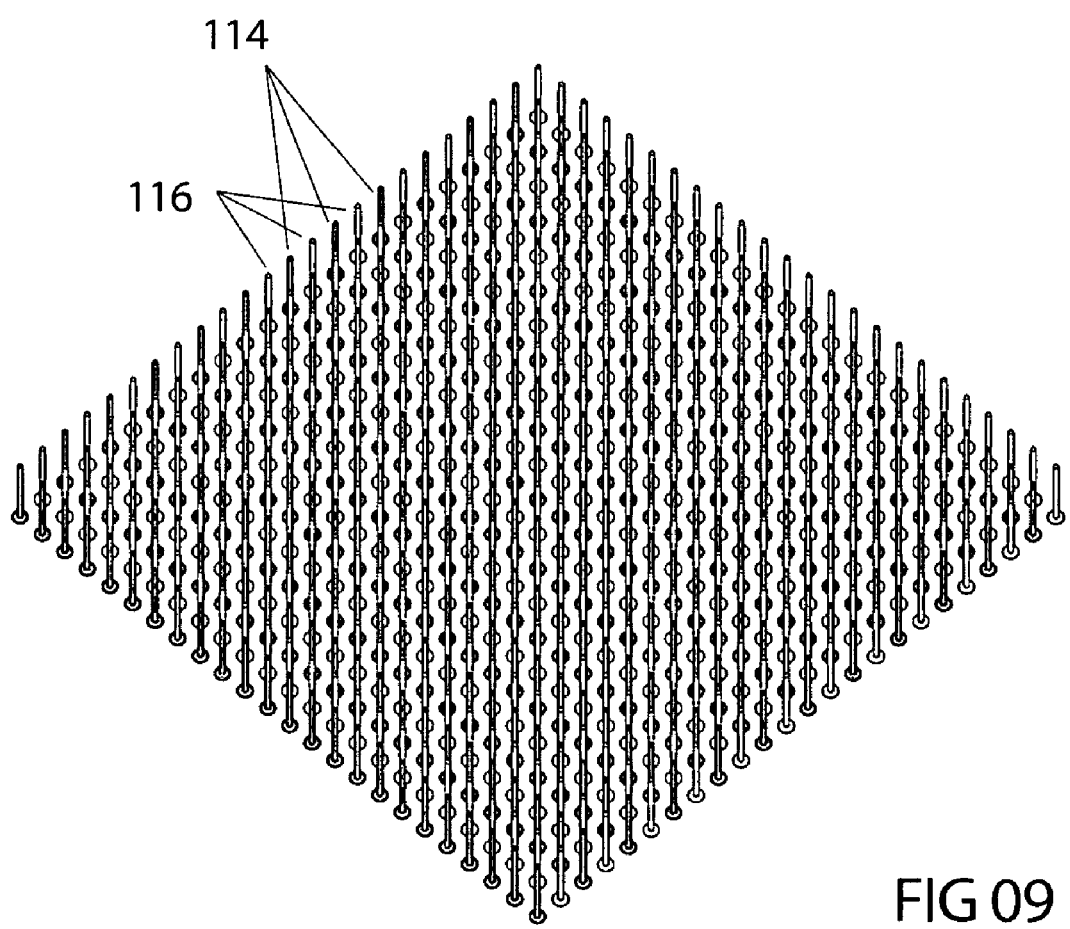
FIG. 09 is a perspective view of an array of points with alternating rows of two materials, ferromagnetic and diamagnetic metals.
Figure 10:
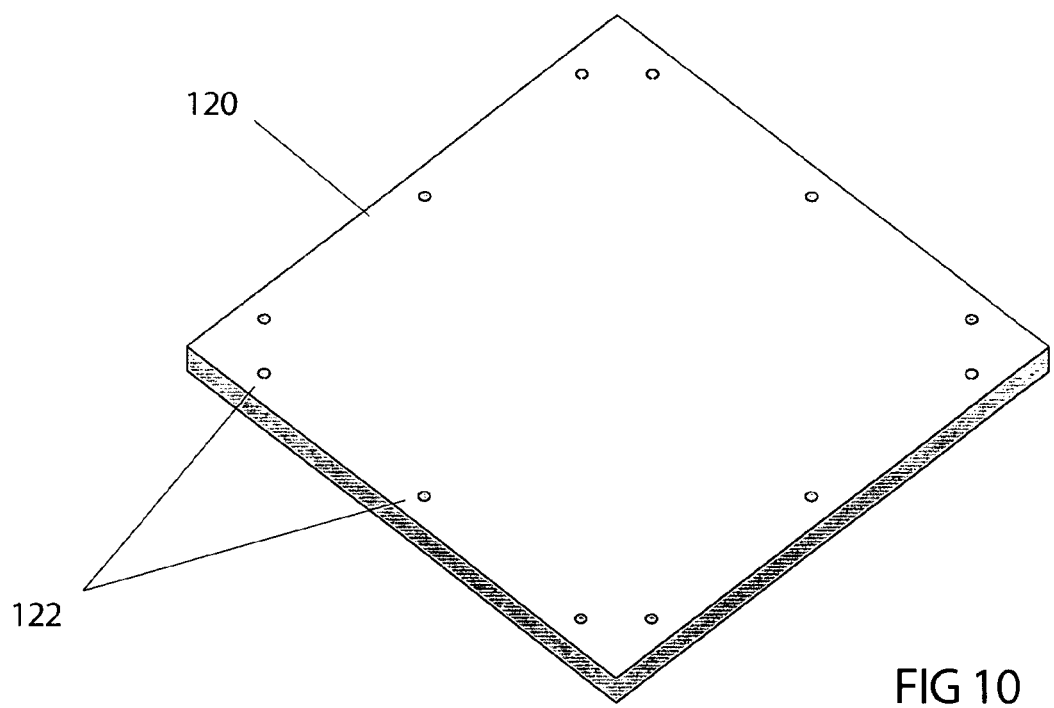
FIG. 10 is a perspective view of a flexible base block with mounting points.

Referring now to FIG. 09, further developments incorporate the galvanic response of a subject's skin to adjacent ferromagnetic 114 and diamagnetic metal points 116 which create micro voltages and currents when connected due to the moist, saline, conductive character of human skin between them. Embodiments that utilize alternating ferromagnetic and diamagnetic points are shown in assemblies 130 and 132 of FIGS. 09-11, 13-15 and 28-30. This phenomenon yields unexpected benefits to broad local regions of a subject differing from those derived from direct stimulation by applying electric current or fields. The inventor has discovered useful coordination of acupuncture treatments and applications of his invention in its passive, galvanic mode that are dramatically effective, e.g., placing the point array in the mid-lumbar region to augment "Kidney Meridian" tonification, and, in another type of acute illness, lower-thoracic placement to augment healing of acute bronchial conditions by means of classic traditional Chinese acupuncture techniques.

A further effect of the mixed ferromagnetic 114 and diamagnetic points 116 is seen in the modulation of the magnetic field arising from the magnetophore base 120 which varies in relative polarity and intensity as it passes from point to point.

Figure 7:
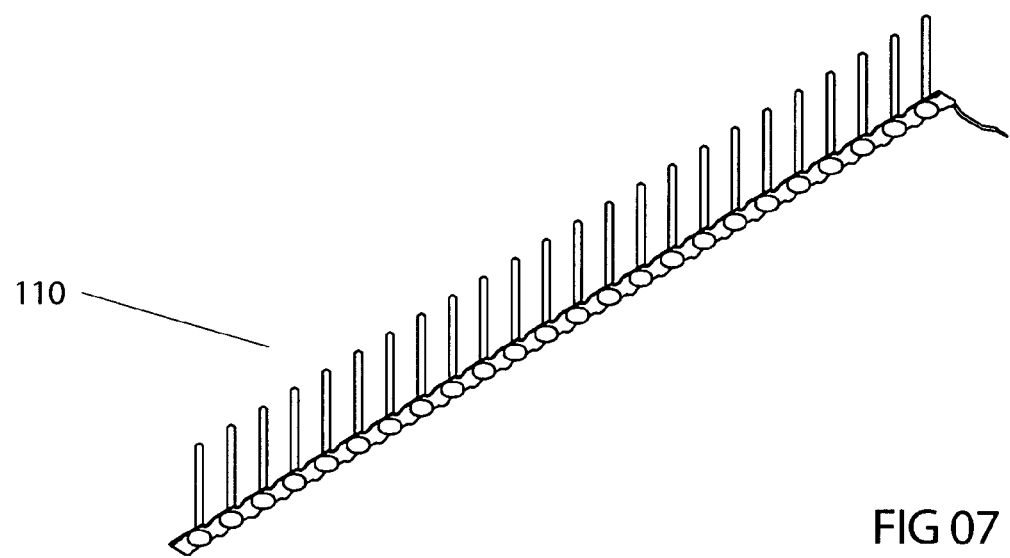
FIG. 07 is a bottom view of the entire point row assembly.
Figure 8:
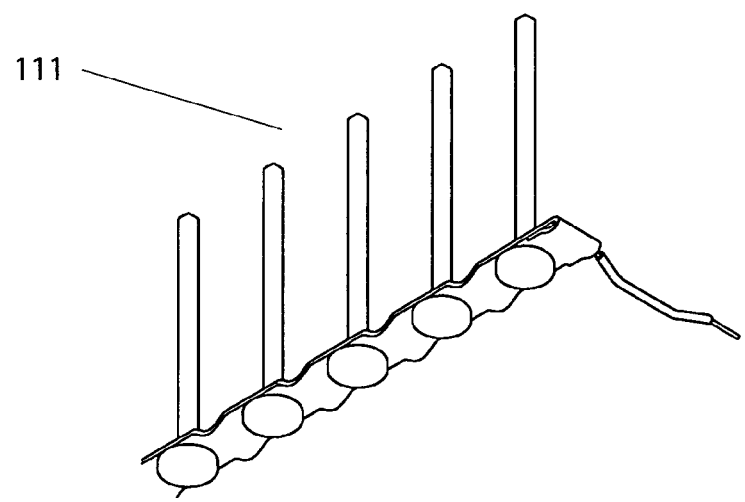
FIG. 08 is a close-up of a portion of the point row assembly.
Figure 11:
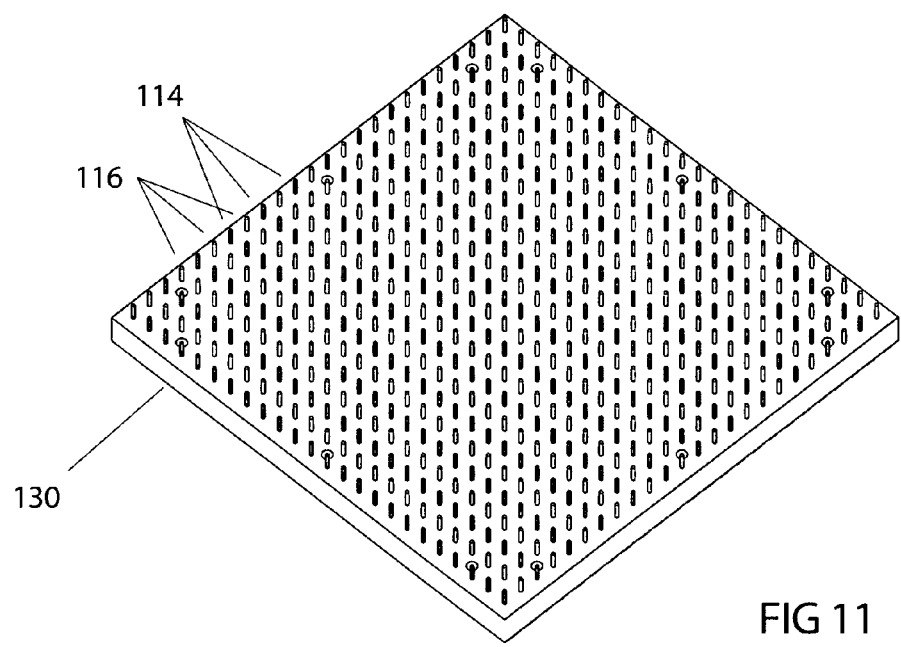
FIGS. 11 and 12 are perspective and side views of point row assemblies in the flexible base block.
Figure 12:
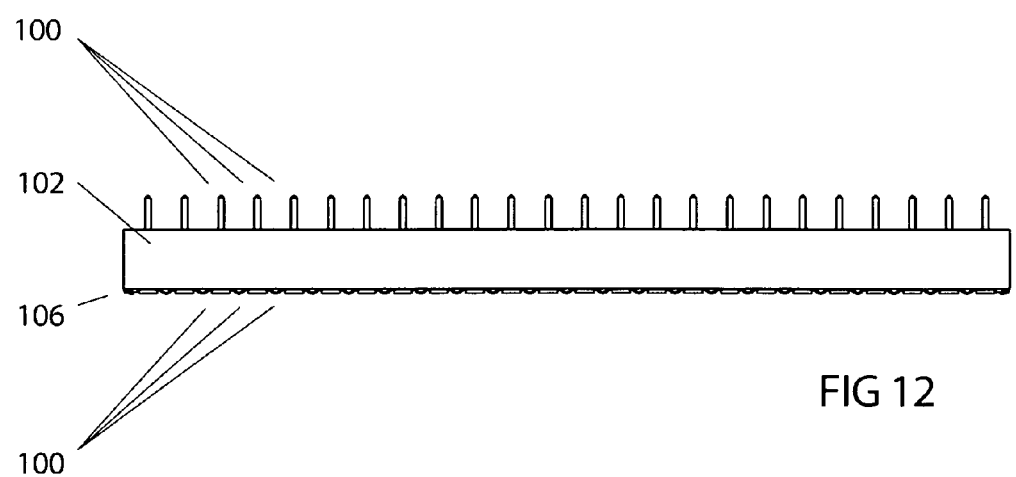
Figure 13:
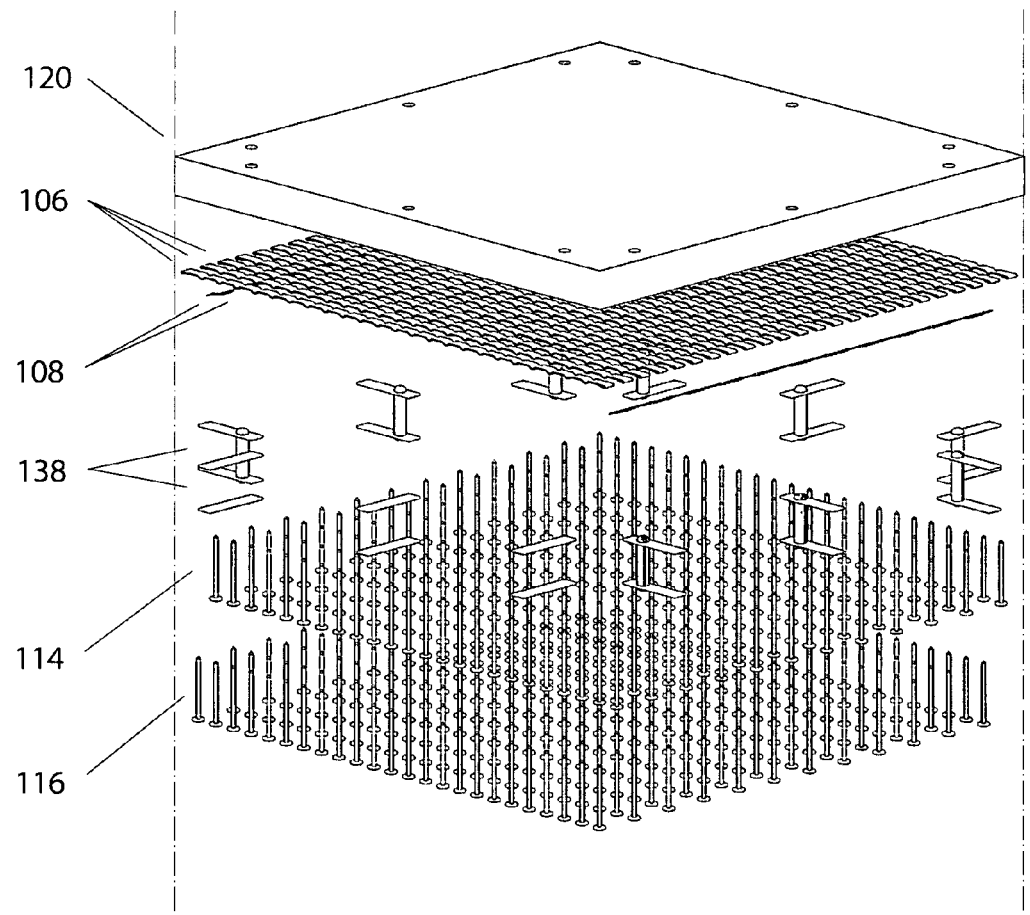
FIG. 13 is an exploded view of a unit point block assembly in accordance with the preferred embodiment.
Figure 14:
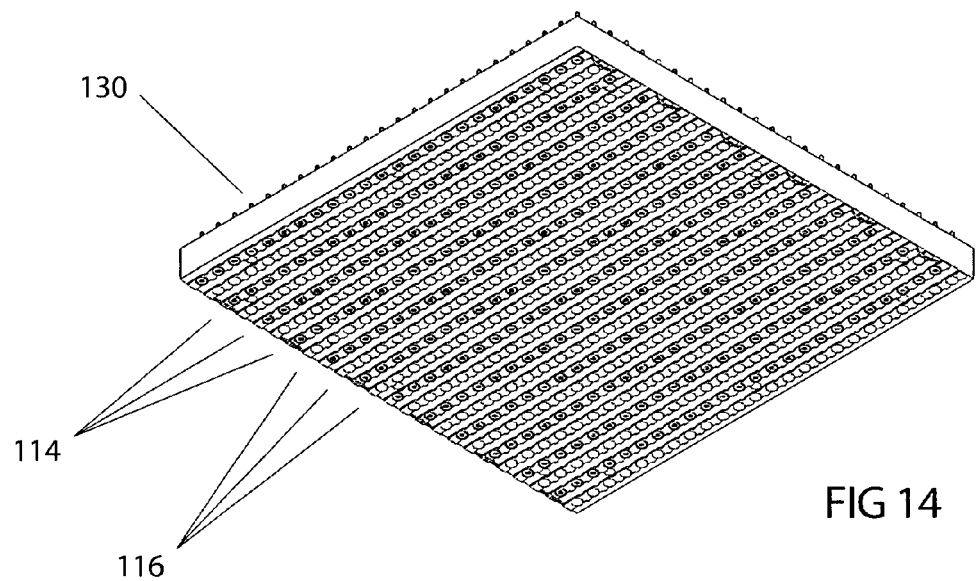
FIGS. 14 and 15 show a bottom view of a unit point block assembly, highlighting the alternating point materials and the conductive strips, respectively.
Figure 15:
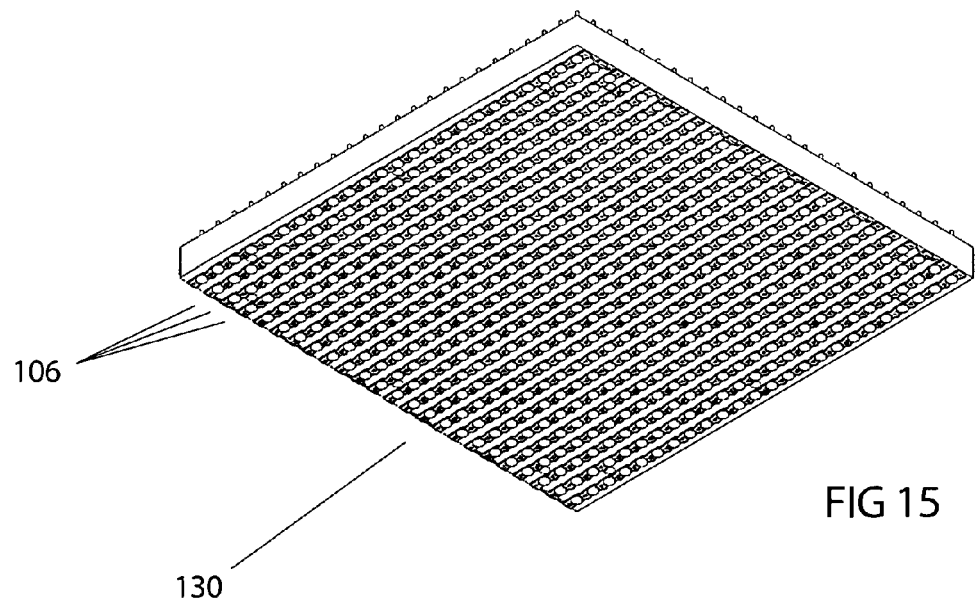
Figure 16:
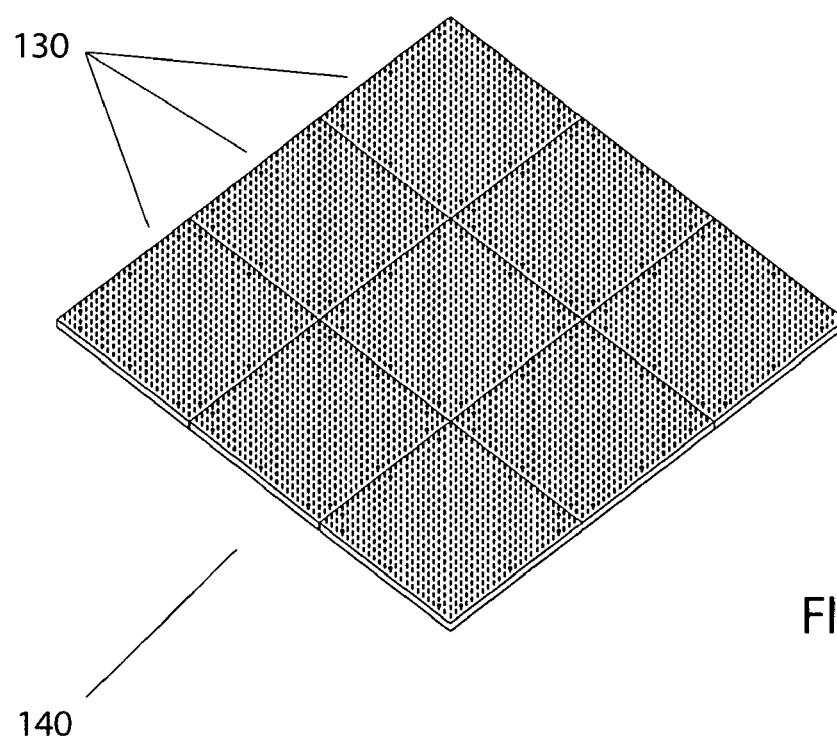
FIG. 16 shows a 3×3 assembly of separably controllable unit point block assemblies.
Figure 17:
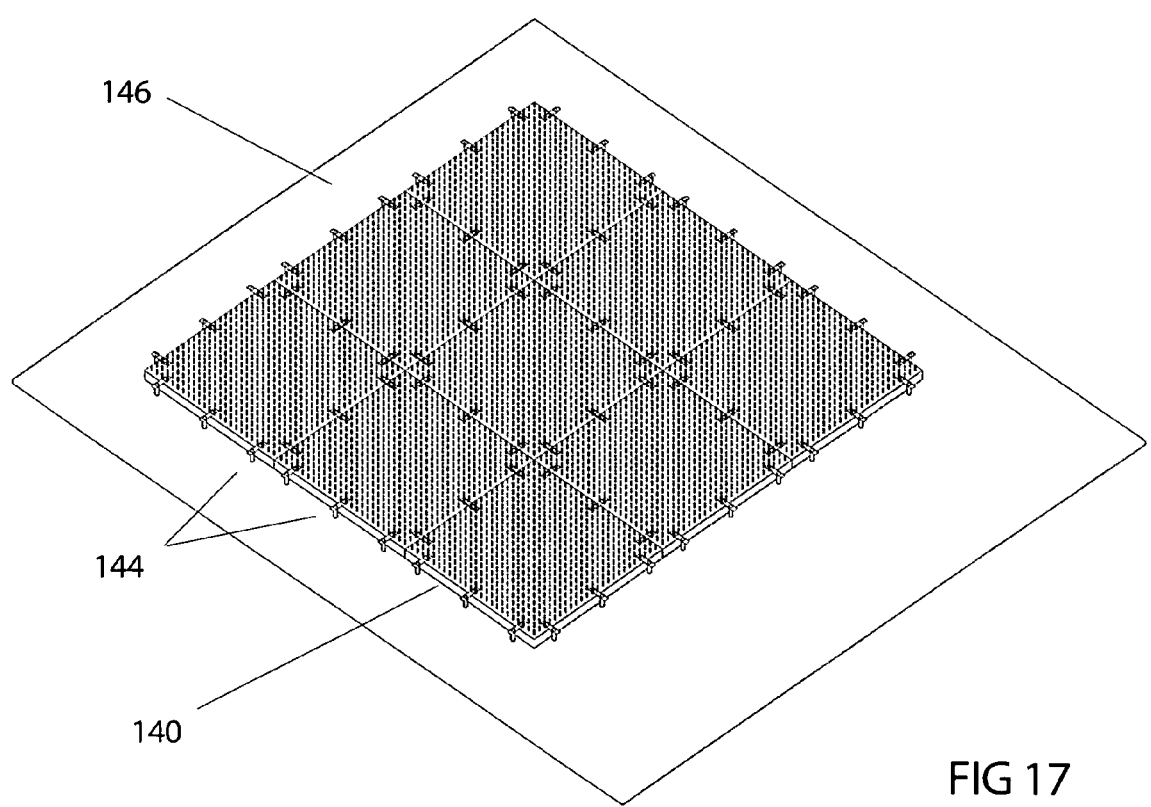
FIG. 17 shows a perspective view of the 3×3 unit block assembly attached to a flexible base (e.g., a sturdy fabric).
Figure 18:
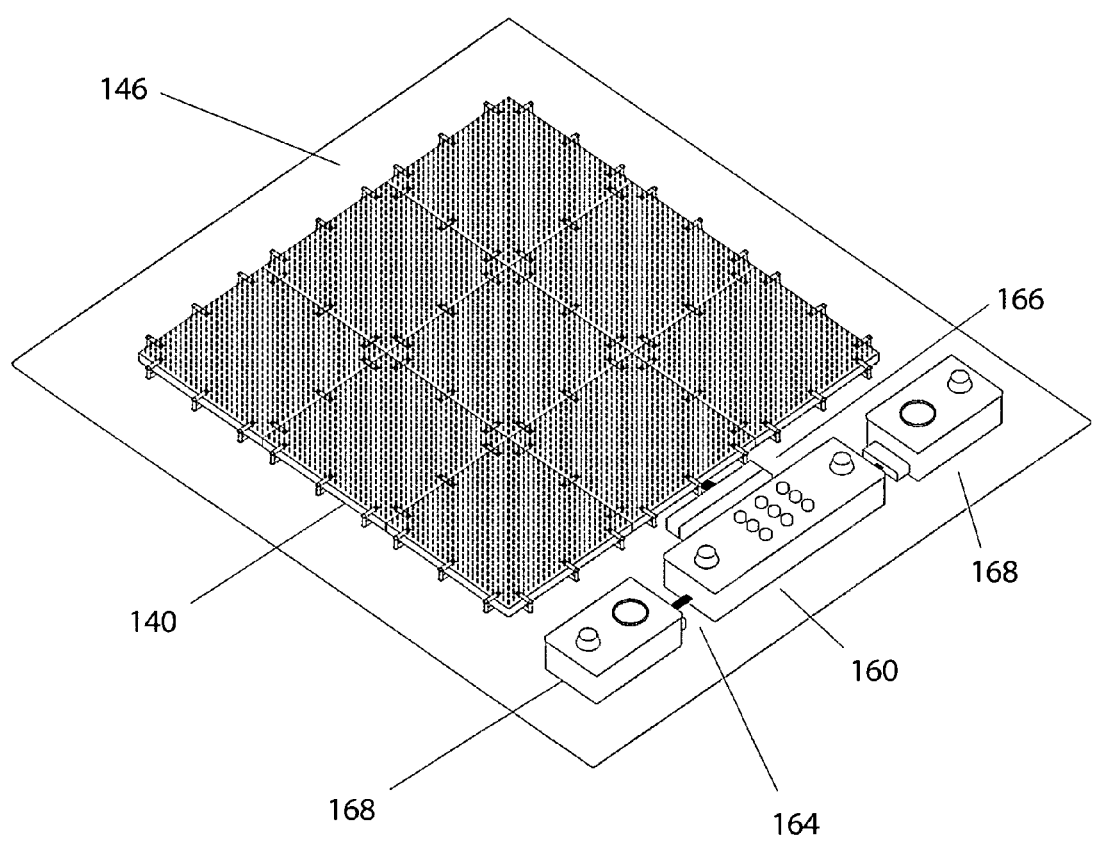
FIG. 18 is a perspective view of the 3×3 unit assembly on its base with electrical connectors to two source modules supplying electromagnetic stimuli through an intermediary adapter module in accordance with the preferred embodiment.
Figure 19:
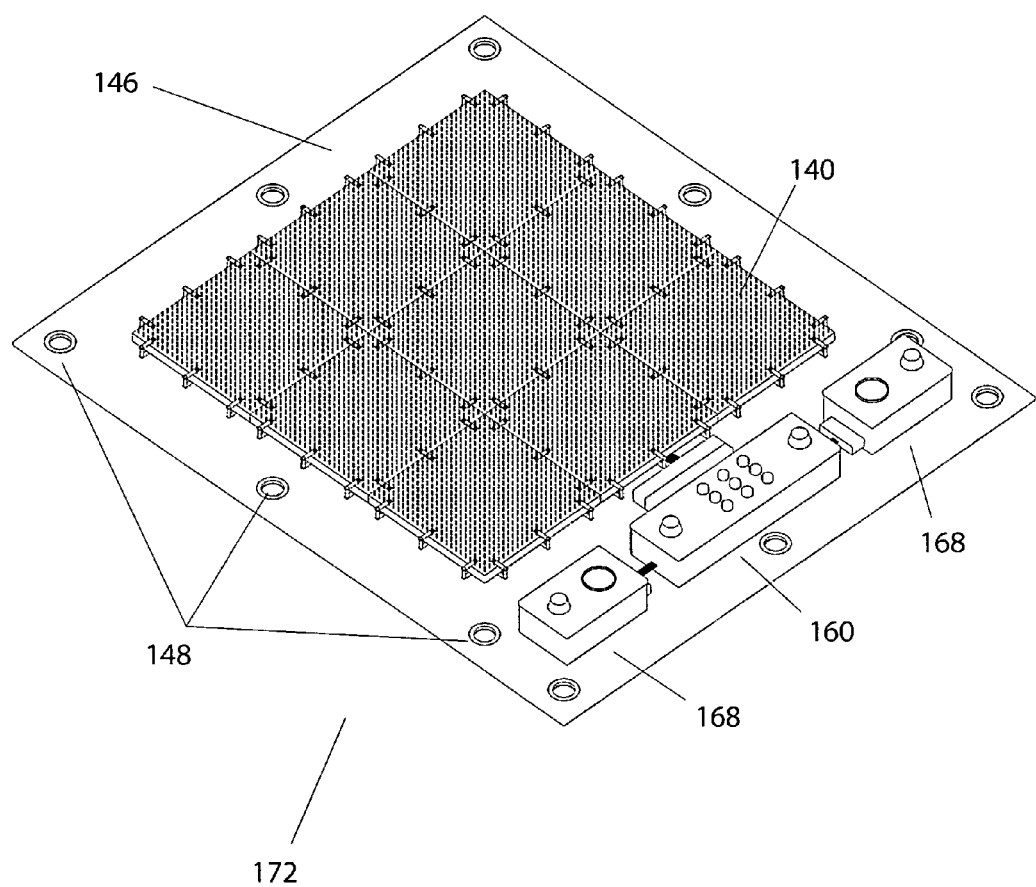
FIG. 19 is an example of a finished operational assembly showing accessory attachment points in the flexible base of FIG. 18.

FIGS. 07 and 11 show one arrangement of diamagnetic points 116 (e.g., brass or copper) and ferromagnetic (e.g., iron or steel) points 114, the arrangement used in the preferred embodiment of this invention. The diamagnetic and ferromagnetic points are in alternating rows, connected within themselves by a conductor and the rows connected with each other by wire leads. For example, FIGS. 04-08 show one row 104 of points electrically coupled by a conductive strip 106 to form a row assembly 110 (partial 111), where a wire lead 108 provides signals to the points. This is shown on a larger scale in FIGS. 12-15. Checkered and hexagonal patterns are subjects of further inquiry for continuing developments of the present invention.

It is hypothesized that this device achieves enhanced effects over or alongside other electrical and magnetic stimulation therapies because the assembled arrays of points 114 and 116 create an effect of a single large field and, simultaneously, the numerous pairs of electrode points create myriad small field changes. The unexpected effect has dramatically enhanced effectiveness of healing responses in a manner quite distinct from other therapies and is capable of beneficially augmenting those therapies.

Indications are that point arrays 114 and 116 at a density of three to ten points per square centimeter (from about 3mm to 6mm apart), show enhanced effects with all types of points and stimuli. Higher point densities have little or no effect ("like lying on a rug"); lower point array densities exhibit little or no effect.

Rectangular arrangements of points are practical to assemble, but further research may uncover advantages for hexagonal or other arrays not further described in this document.

Current research indicates that the points 114 and 116 should be sharp, or nearly so, to most effectively induce and modulate electromagnetic fields. In practice, this device has not caused problems in which sharp points puncture, lacerate or abrade a subject's skin. Transient minor discomfort, a sensation of "roughness," is common. Flushing, i.e., localized redness and warm sensation characteristic of increased blood flow, accompanying and following treatment is seen as a practical indicator of effectiveness.

An advance in the development of this device incorporated magnetized material into the point block supports 102 or 120 (FIGS. 02, 03, 09-15, 27-30). The combination of an array of points with a broad magnetic field potentiates the magnetic forces much as the electrical fields. On one hand, the point arrays create a wide active field and on the other, they create alternating gradients of field strength and field orientation between adjacent points.

This important combination of a magnetized support 102 or 120 and arrays of alternating diamagnetic points 116 and ferromagnetic metal points 114 is referred to as the unit point block assembly 130 or 132 (FIGS. 11-15, 28-30) shown in the preferred embodiment of the present invention.

Assembling these unit blocks 130 into arbitrarily larger arrays 140 and 142 is easily accomplished with fasteners that allow flexibility across the whole device. FIGS. 16-21 illustrate one possible sequence of steps for assembling a functional device. Operational assemblies 172 and 174 incorporate these combined units 130 with a flexible base 146, fasteners 144, connectors 164 and 166 and attachment points 148 for power supplies, other components 160 and 168, and accessory layers. Easily layered accessory components 178 and 180, such as heating pads, and enhanced magnetic field sources (permanent magnets 184 in FIG. 22) can be used as desired, merely by employing mounting openings that include grommets 148 and 150.

Operational Modules

Therapeutic devices may apply up to 10 volts DC to a subject. Galvanically induced micro currents and their potentiation by the point arrays of the illustrated embodiments present the other extreme of intensity useful in this device, a very wide range. Many different forms of electrical current and electromagnetic fields are known to be useful or possibly useful.

Accordingly, it is important to accommodate the optional use of differing source modules 168 and 170 of FIGS. 23-26 or the use of none. The adapter modules 160 and 162 in embodiments of this invention attach to any of the source modules and to the built-in wiring harness of the point block arrays, switching between optional source modules and local galvanic effects in a variety of combinations.

For safety and reliability, all circuitry must be designed to isolate users from any possible harmful electrical currents, and unwanted electro-magnetic frequencies. A combination of isolation circuitry and fault-responsive circuitry is incorporated accordingly and maintained at appropriate industrial, consumer and medical safety standards.

Adapter Modules

Referring to FIGS. 18-21 and 23-25, electromechanical adapter module 160 is electro-mechanical in operation and permits manual switching of individual point block assemblies 130 and 132 in the array between source modules 168 and 170, galvanically induced currents, or open condition (no current flow). Unit blocks function in parallel when connected to a source module, including galvanically and environmentally induced loads, unless serialized by a suitably configured source module. Each block switched to "self" (the middle throw of the block's three position source selector switch 208 of FIG. 25) has its separate galvanically and environmentally induced current.

Figure 26:
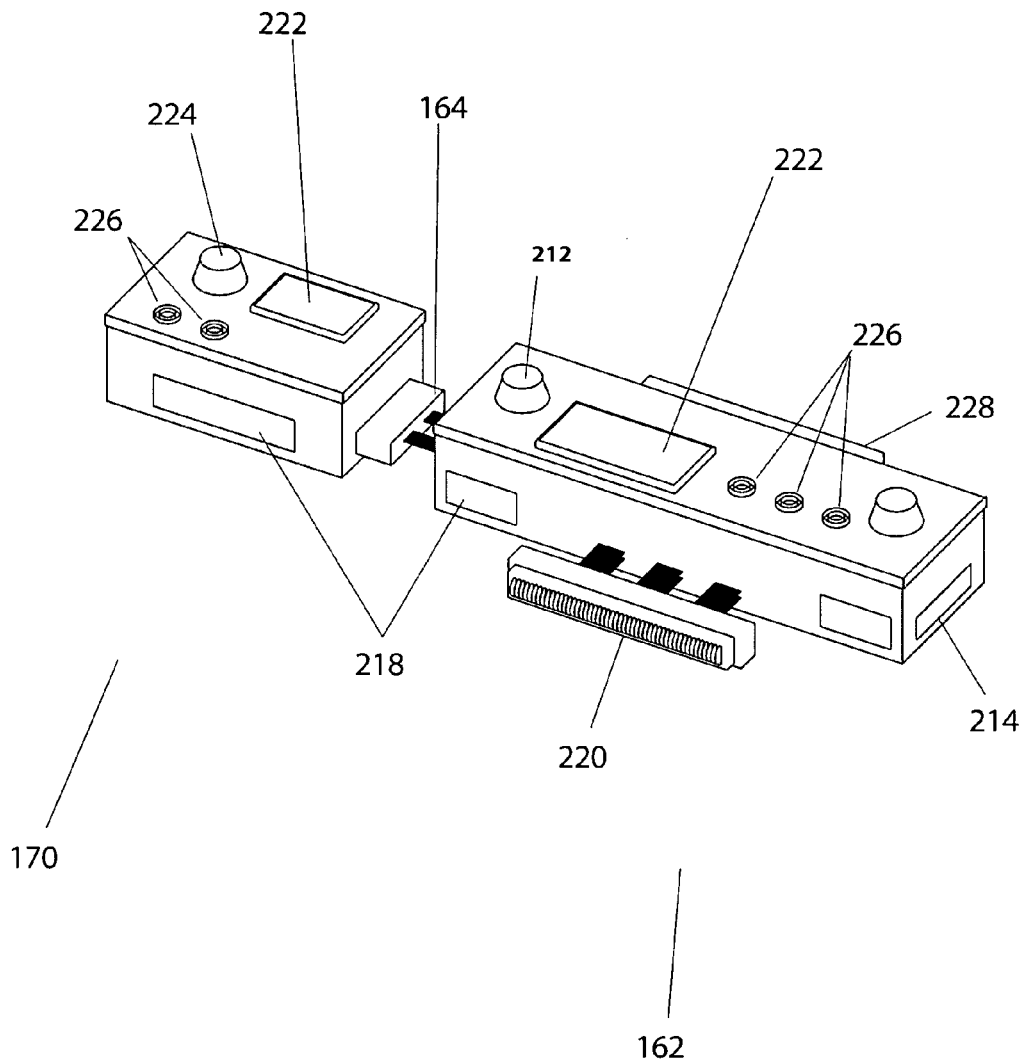
FIG. 26 is a perspective view of a 3×3 data and real-time adapter module with a data source module, permitting simultaneous monitoring and control of each point block separately.
Figure 27:
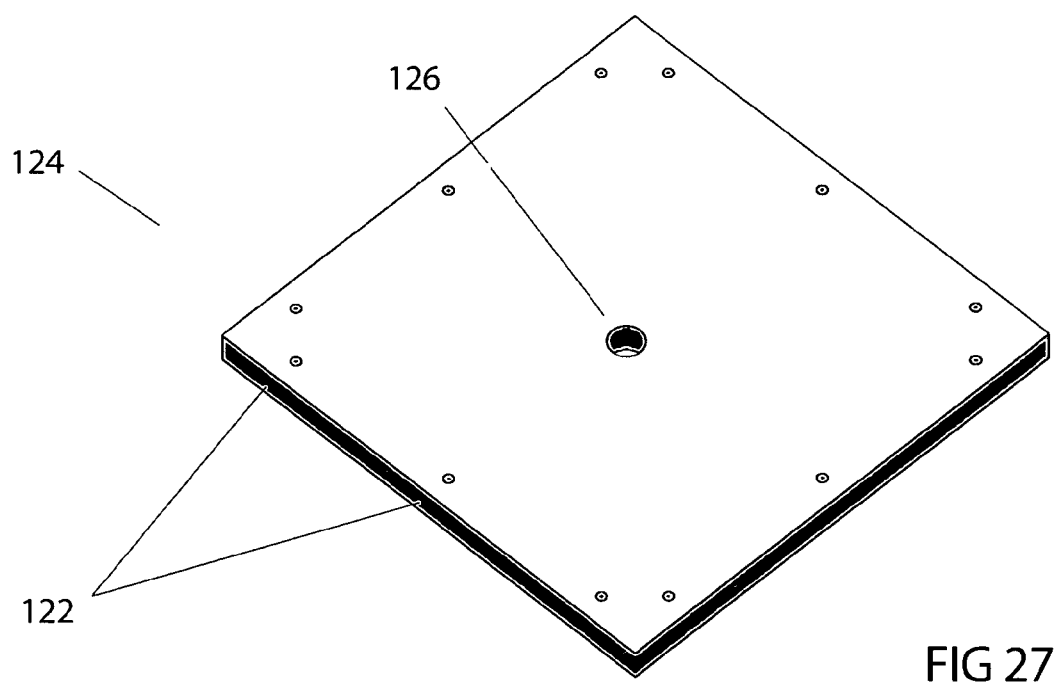
FIG. 27 shows the alternative embodiment support block. The opening in the flexible base accommodates a mounting fixture for accessories including hypodermic needles, topical medicinal applicators, and sensors to monitor physical parameters such as temperatures, or electromagnetic and galvanic conditions.
Figure 28:
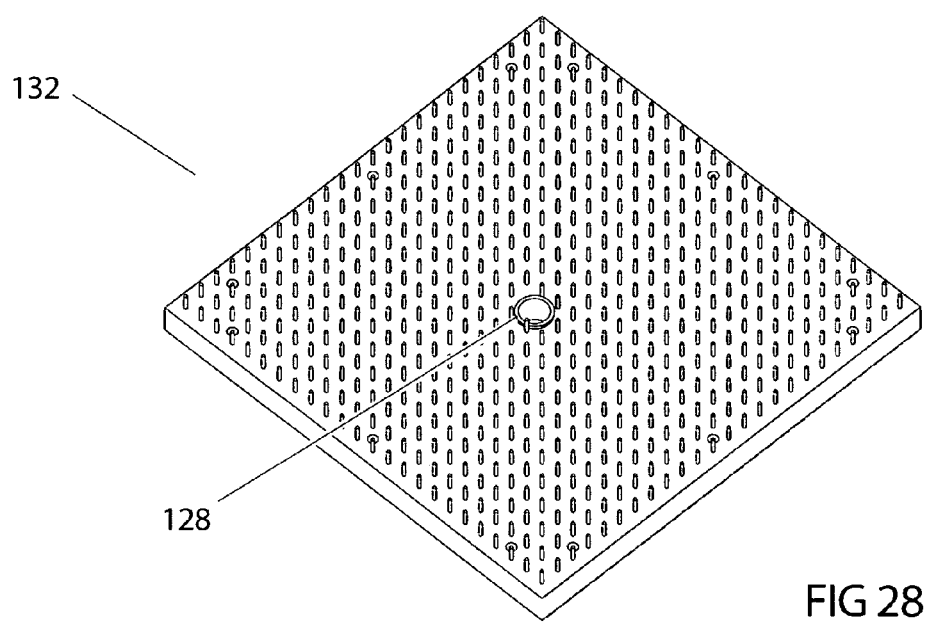
FIGS. 28 and 29 are upper and lower perspective views of an alternative embodiment unit point block assembly.
Figure 29:
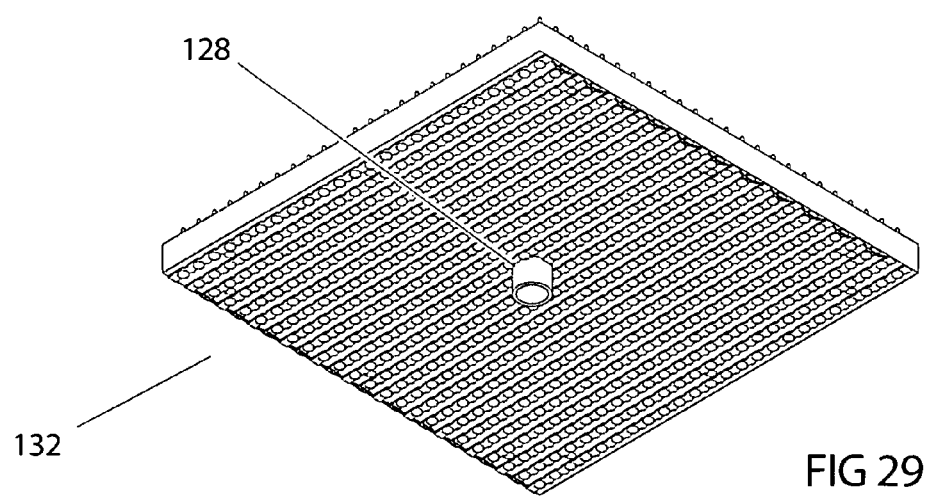
Figure 30:
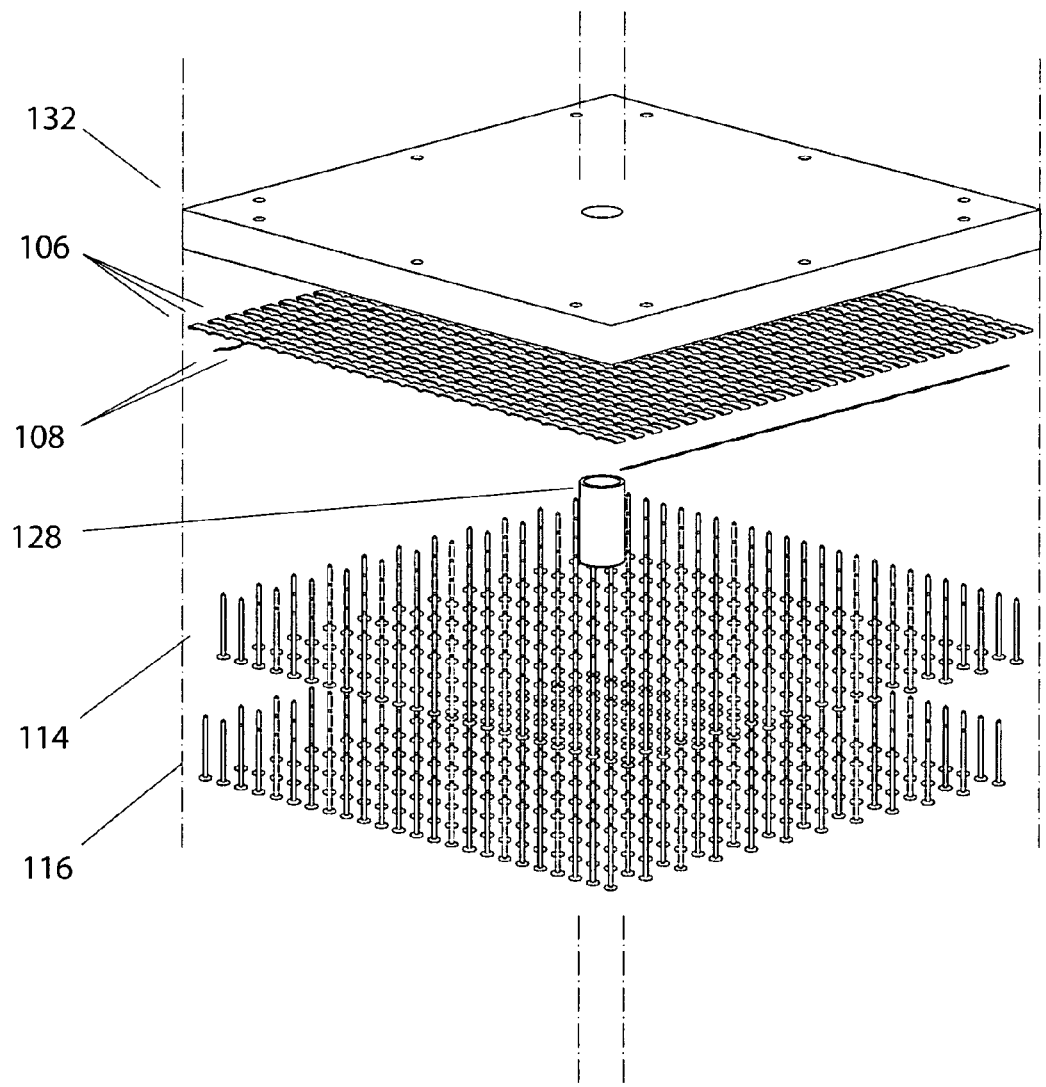
FIG. 30 is an exploded view of a unit point block assembly of the alternative embodiment.

A data and real-time adapter module 162 of FIG. 26 permits external devices to simultaneously monitor, drive or control each point block assembly. This direct or indirect data and control interface enables one or multiple analog circuits through a multi-circuit analog port 228 or digital data via integrated digital controllers through input/output ports 226. It employs commercially available integrated circuits, controller boards, and operating systems. The arbitrary number of circuits available to each point block is limited only by practical considerations. Also shown in FIG. 26 are a function selector switch 212, a multi-circuit jack 214 for source module connections, attachment points 218 for connection to the flexible base, a connector plug 220 to unit blocks, a metering and status display 222, and a variable control 224.

Source Modules

Source modules can function self-contained or can be powered by battery, piezo-mechanically, or otherwise externally powered. The source can provide current flows or static potentials. These can be of direct or alternating polarities, continuous or discontinuous, uninterrupted or interrupted, unmodulated, frequency modulated, or amplitude modulated, unvaried, randomly, or regularly varied, as possible and as suitable. Variants may be manually, programmatically, limit, or feedback controlled and incorporate appropriate sensors.

Figure 23:
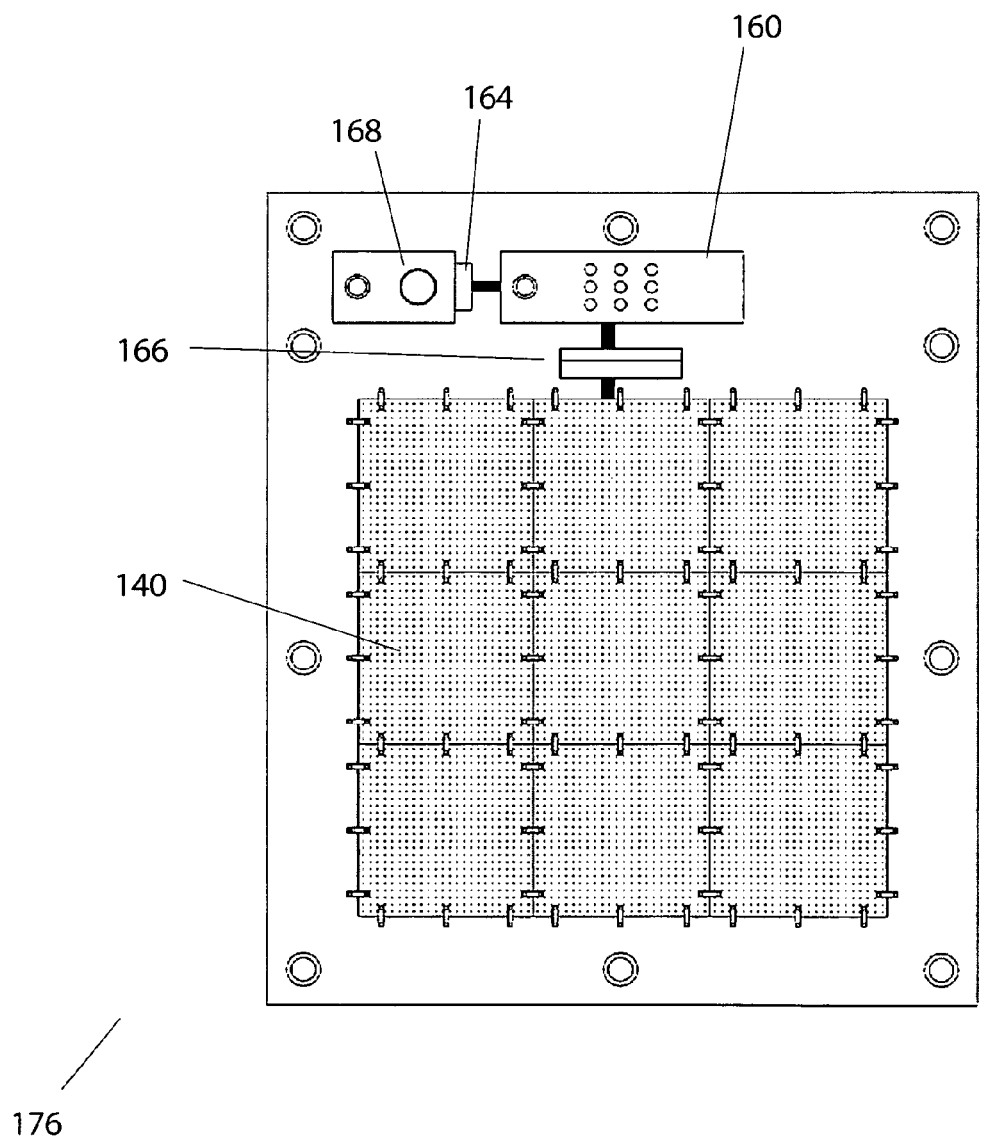
FIGS. 23 and 24 show top views of an electromechanical adapter with one and two source modules, respectively, attached to the preferred embodiments of this invention.
Figure 24:
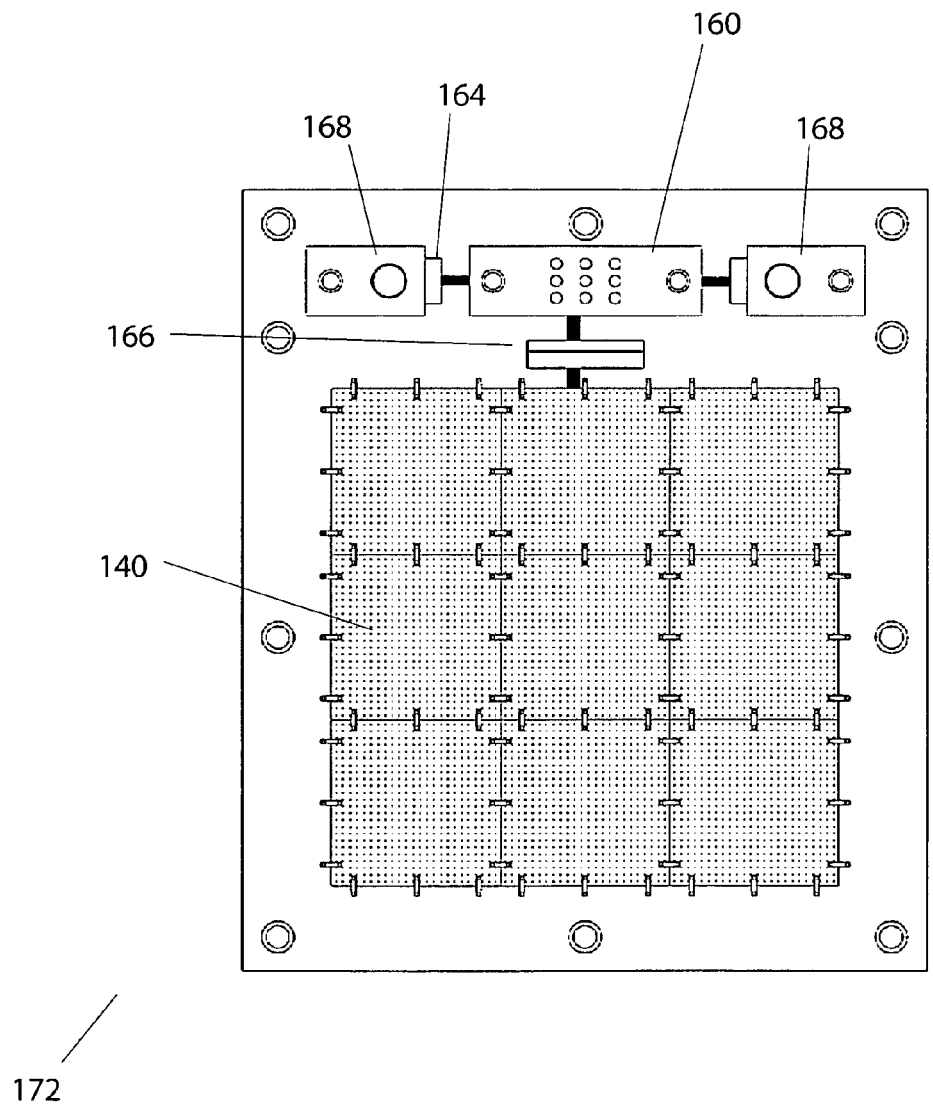
Figure 25:
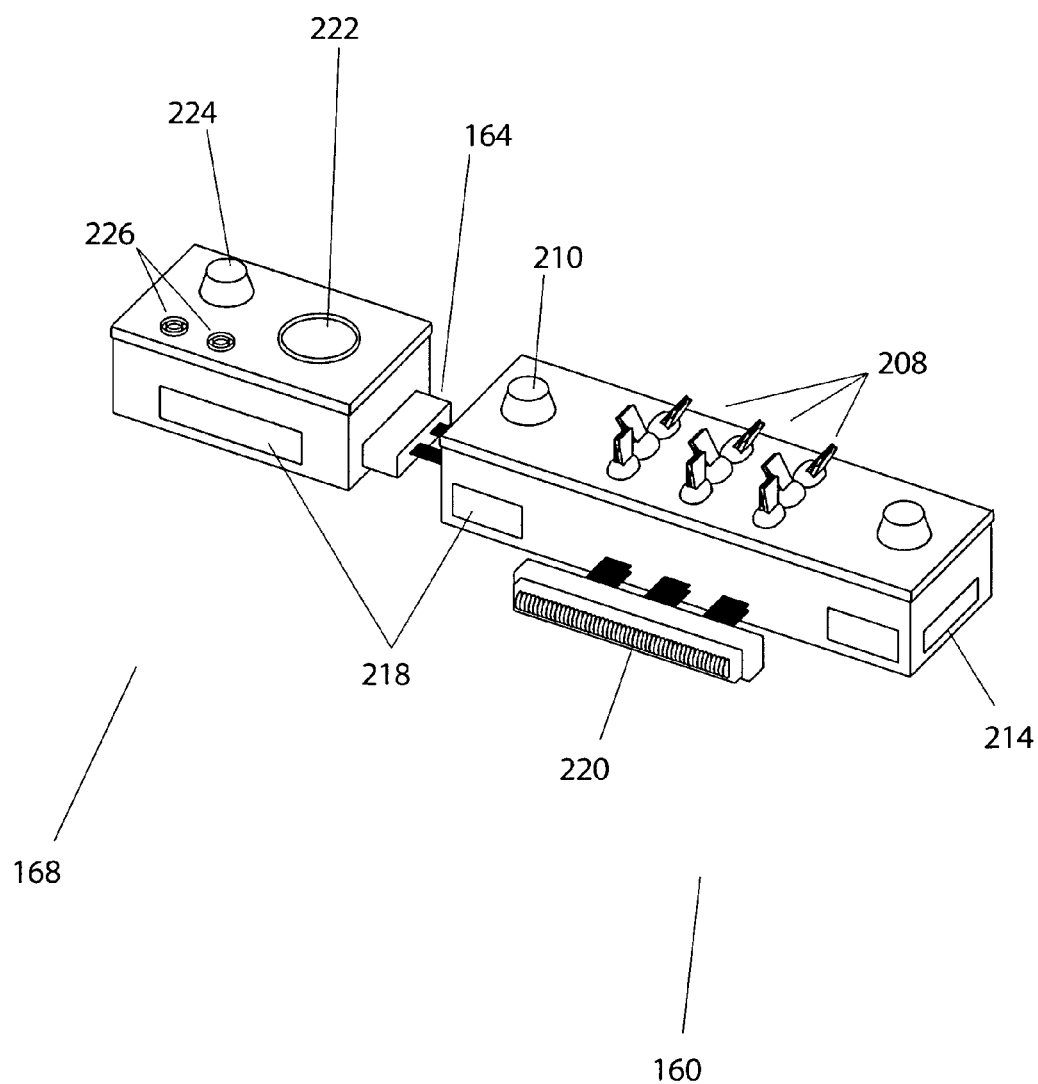
FIG. 25 is a perspective view of a standard electromechanical 3×3 adapter module with one source module.

The parallel-circuit source modules 168, such as shown in FIG. 23, are designed to operate on unit blocks as proposed in the preferred alternative embodiments.

Addressable-control source modules 170, such as shown in FIG. 26, are used with the data and real-time adapter modules 162. The circuitry of each addressable control source module communicates with, controls or is controlled by external controllers through input/output ports 226, and also communicates with the adapter module 162 via the source module connector 164. Embodiments of this invention may employ very fine degrees of control and monitoring down to the individual point level through appropriately wired unit assemblies.

Self-metering or externally controlled sources can maintain continuous or programmatically defined levels of stimuli based on simultaneous monitoring of the point arrays themselves.

Attachable Accessories

Figure 20:
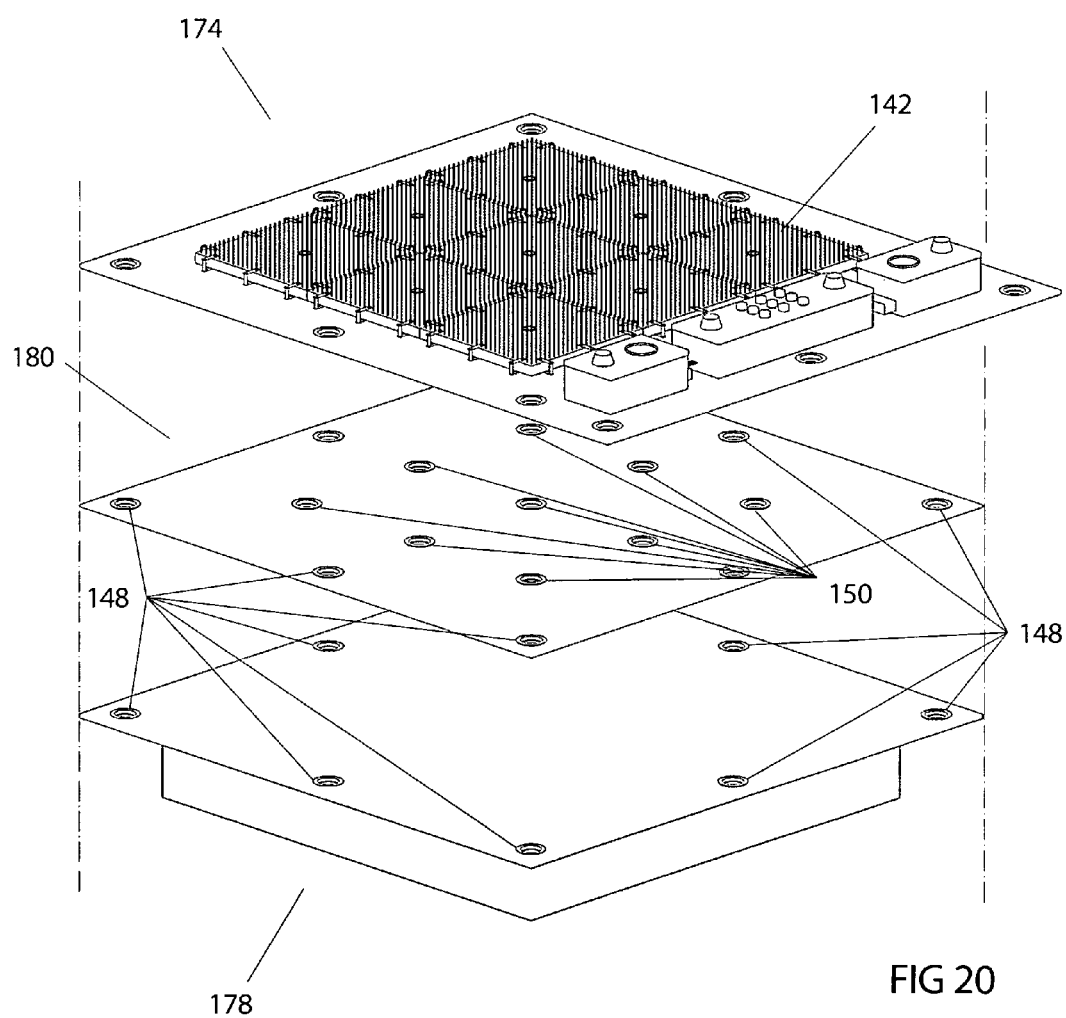
FIGS. 20 and 21 are exploded and perspective views of an operational assembly, in the alternative embodiment, with two attachments. A visco-elastic pad attachment is usually employed with both embodiments. Optional accessories fit between the operational assembly and its visco-elastic pad attachment.
Figure 21:
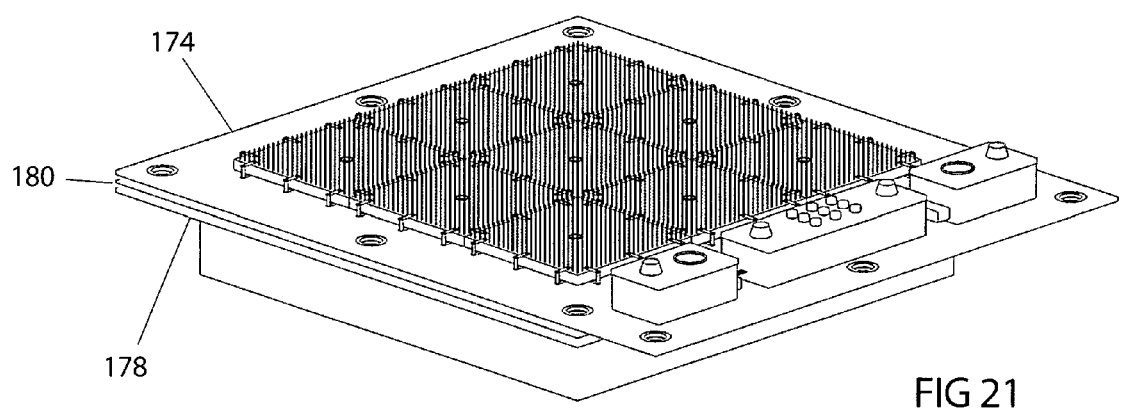
Figure 22:
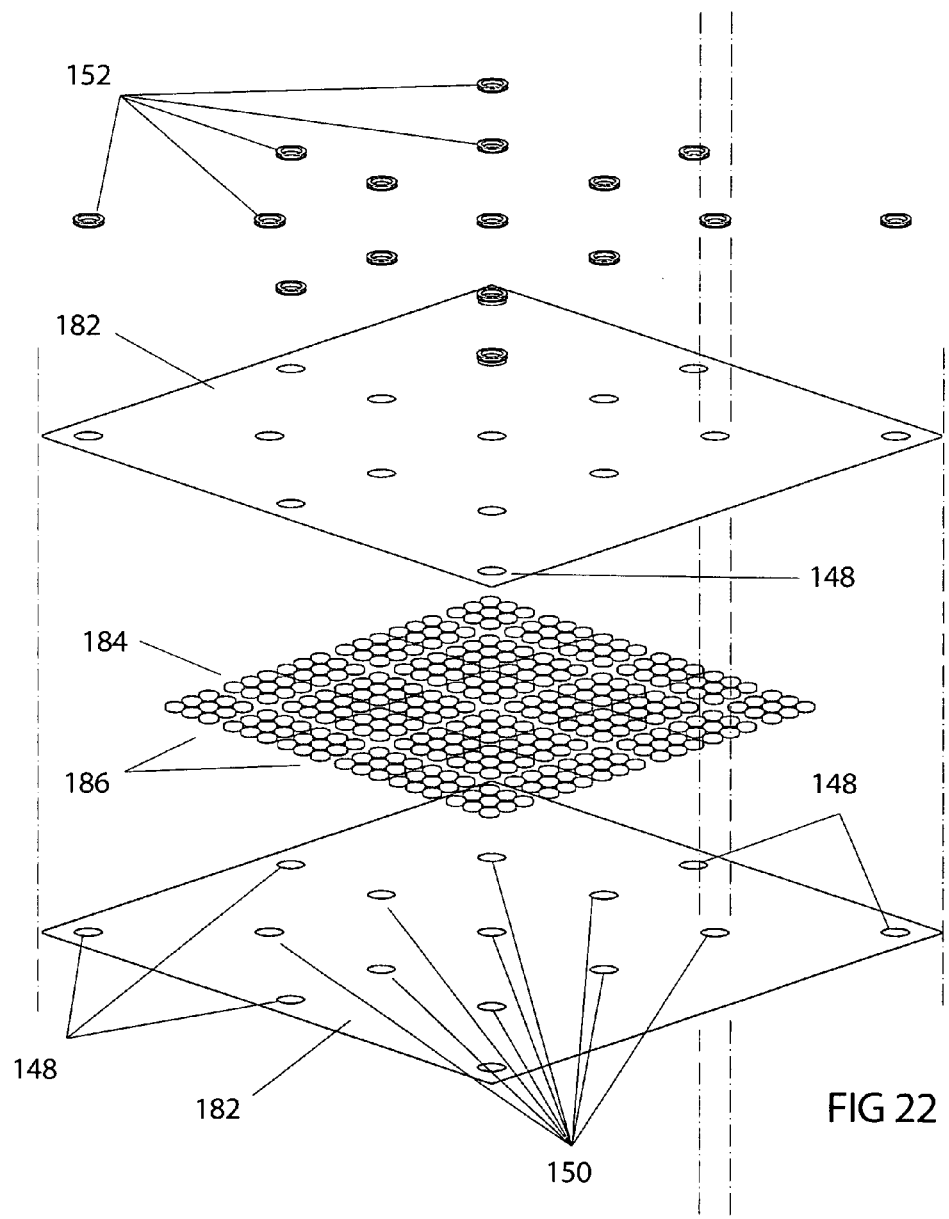
FIG. 22 is an exploded view of a typical attachable accessory, in this case providing supplementary magnetic fields by means of permanent magnets. Access holes and gaps within the accessory assembly make it fully compatible with both the preferred and the alternative embodiments of this invention.

Accessory attachments 180 of FIGS. 20-22 outwardly resemble one another except for attachments and connectors, such as electrical wires or tubes and except for varying thicknesses. One or more accessory attachments 180 can be layered between an operational assembly 172, 174 and 176 and the visco-elastic pad 178 to provide supplementary stimuli, including electrical or magnetic fields, physical vibration, and heat or cold.

The attachment points are holes or integrated fasteners 148 which align the layers. Grommets or other reinforcements 152 may be included to strengthen the attachment points.

Alternative Embodiment

The alternative embodiment of FIGS. 27-30 differs from the previously described embodiments in one respect. Each unit block 132 includes an opening 126 fitted with a clinical accessory mount 128 designed to securely hold devices such as hypodermic needles, topical applicators, acupuncture needles, or sensors connected through a tubing or wiring harness to external devices. In the case of hypodermic or topical injectors, the external device may be standard medical drip bags or pumps. Devices such as acupuncture needles would be connected as needed to standard power sources now in common use by practitioners in the field.

In FIGS. 20 and 22, accessory components 180 and flexible supports 182 of the system incorporate openings 150, allowing access to the clinical accessory mount on each unit point block of the alternative embodiment. The components within each accessory are arranged with gaps 186 that permit tubing and wiring harnesses to run unimpeded and be well protected. Simple grommets 152 or specially purposed fasteners may be used to reinforce and/or align these openings.

From the description above, a number of advantages of the present invention become evident:

A. Novel and unexpected therapeutic benefits arise when point arrays in the specified range of spacings apply physical stimuli to areas of a subject's body, especially in flexible, planar arrangements of ferromagnetic and diamagnetic points in magnetized supports alone and with optional field sources as seen in the preferred embodiment of this invention;

B. Because the assemblies are relatively thin, they permit application of a wide variety of stimuli and intensities, singly or in arbitrary combinations, through accessory attachments;

C. The flexible and modular design of this invention accommodates needs for portability and simplicity of operation in the field in the preferred embodiment. It accommodates intensive use of invasive procedures, bulkier accessories, and complex control systems in clinical settings in the alternative embodiment. Finally, ongoing clinical and scientific research into phenomena related to the use and effectiveness of the invention are facilitated by easy integration of monitoring, sensor, and control systems; and D. This invention offers therapeutic opportunities that relate to an unprecedented range of healing arts traditions and medical disciplines, including allopathic medicine, physical therapy, sports medicine, therapeutic massage, traditional Chinese medicine, folkloric medicine, naturopathies, herbalism, and others.

Operation of the Preferred Embodiment

Referring now to FIGS. 19-21 and 23-26, operation of this invention is typically by application of the active side to a surface of a subject's body. This is commonly achieved by first assembling an operational assembly 172, 174 and 176, including an adapter module 160 and 162 and one, two, or no source modules 168 and 170, with optional accessories 180 and the visco-elastic pad attachment 178. This combination is placed on a firm surface, such as a massage table. The subject then lies upon or reclines against the active side of the device.

The point arrays 100 and the subject's surface are deformed by their mutual contact so as to exert a relatively uniform pressure over the area of contact. The elasticity of human skin ensures that even very sharp points 100, 104, 110, 112, 114, 116, 122, 124, 130 and 132 do not puncture it. Subjects report little or no discomfort from the contact.

An adapter module 160 and 162 is required for operation of the preferred and alternative embodiments described in this application. The electromechanical adapter module 160 permits each unit block 130 and 132 to be switched to a closed circuit condition, permitting electrical potential or current flow from galvanic action induced by the adjacent ferromagnetic 114 and diamagnetic points 116 contacting the subject's skin.

The adapter modules 160 and 162 further allow each unit block 130 and 132 to be switched to one of two circuits which can be open (no current flow) or closed by an attached parallel source module 168. The source modules may induce electrical currents or potentials of any physical nature possible. They may provide simultaneous metering of electrical conditions between the two sets of connected points in the connected blocks, or they may allow simultaneous metering of those conditions as responsive changes are created in the subject.

The electromechanical adapter module 160 has source on-off-option switches 210 with nine poles and three states. The states set the connected blocks open (no current), closed to themselves (galvanic effects in parallel) or connected to the source module plugged into its connector 164. More elaborate versions of the electro-mechanical on-off-option source switches 210 accommodate differing combinations of effects and metering through multiple circuits and switch states.

The data and real-time adapter module 162 provides a digital interface 226 and an analog interface 228 to the unit blocks 130 and 132 and controllers built into the adapters themselves. With these adapters, computer-based, algorithmic or automatic controls may be designed and built as needed for therapeutic or research goals. Displays 222, e.g., LED readouts, can optionally provide direct information apart from attached computers or other devices regarding the state of elements within, attached to, or affected by the adapter module.

Addressable control source modules 170 may be used with the data and real-time adapter modules 162. The circuitry of each addressable control source module communicates with, controls, or is controlled by internal components, adapter module controls or external devices. They may generate, monitor, or modulate electromagnetic forces severally and in combination, limited only by the granularity of the connections to the point arrays and circuitry connecting them with those point arrays.

Once the subject and the device have been placed in contact, the switch settings on the adapter module 160 and 162 are set in accordance with the effects or monitoring desired.

Setting source selector switches 208 on the electromechanical adapter 160 to the center position allows galvanically induced micro-currents to flow within each unit block 130 and 132. Setting some number of the source selector switches to one of the source on-off-option switches 210 allows those blocks to be disconnected (open circuit), their galvanically induced micro-currents to flow in parallel as one circuit, or connected to an attached source module. That source module can then provide some induced effect, monitor electromagnetic conditions, or both. Settings are revised as desired during a course of treatment or observation.

Operation of the Alternative Embodiment

Referring to FIGS. 20-21 and 27-30, the single difference between the preferred (portable) and alternative (clinical) embodiments of this invention is the incorporation of a clinical accessory mount 128 in each unit block. This mount securely latches an injector, applicator, or sensor in place.

The additional step of attaching devices to the clinical accessory mounts 128 precedes assembly of the operational assembly with its attachments. This invention allows for their use during the subsequent course of treatment or observation.

CONCLUSION, RAMIFICATIONS AND SCOPE

Accordingly, the reader will see that this invention incorporates new and novel technologies for therapy and biomedical research.

A. First, its use of point arrays of specified densities offers a broad subject area, non-invasive and gentle therapeutic stimulus that functions in novel and unexpected properties in comparison with point arrays at lesser densities.

B. Metal points mixing ferromagnetic and diamagnetic materials create galvanic micro-current therapeutic stimuli.

C. Mixing ferromagnetic and diagmagnetic materials in point arrays greatly potentiates the effectiveness of magnetic field stimuli.

D. The point arrays similarly potentiate applied electromagnetic stimuli in ways not observed by the single point sources employed in other therapeutic devices;

E. Heretofore separate modes of therapy are combined in a practical, expeditious and unprecedented manner.

F. The modular and extensible design is adaptable to portable field use and to intensive clinical use. Its extensibility accommodates heretofore unexplored subjects of quantifiable scientific research through sensors and control systems already developed and yet to be developed.

Embodiments which are not illustrated may incorporate more complex and detailed circuitry to extend their functionality. For example, the source modules, adapter modules and the arrangement of connections between points can each vary from embodiments that affect all points together (in parallel) to the other extreme of separately monitoring and controlling arbitrary groups of individual points severally or together for forces, sensors and controllers of arbitrary degrees of complexity. It is anticipated that this characteristic architecture will permit research and therapies unprecedented in their scope.

Digital technology permits active addressing, control and monitoring of any arbitrary groups of points, sources and conditions, limited only by the physical construction of the point arrays and circuitry. The element of change over time, especially changes responsive to a subject's conditions, is another ramification implicit in this invention's architecture.

An alternative, simpler embodiment of this invention, not illustrated, is possible in which the alternating point rows in each unit block are directly connected ("shorted"). This embodiment would permit always-on galvanically induced micro-current flows. An alternative, low-cost adapter module that sets this always-on condition in the proposed embodiments is comprised of a connector plug closing each unit block's circuit at the jack.

Three possible types of accessory heat sources (not illustrated) are (a) a convenient electrical pad connected to household power, (b) a portable, liquid-filled, stoppered bladder suitable for chemical reaction heating or cooling, and (c) a pressurized liquid system utilizing a separate heater and pump to circulate temperature-controlled substances through a tubes-and-bladder system. The electrical heating pad and portable bladder types are appropriate for portable uses. Pressurized accessory heaters are suitable in a clinical setting.

Accessory magnetic field boosters covering localized or wide areas may utilize permanent magnets (as in FIG. 22) or electromagnets driven by external power supplies.

The types of arrays of points vary within the scope of this invention. Arrangements of points may be non-planar, nonuniformly sharp or dull, or randomized by material or location. Points may be non-parallel to each other. Points may not hold fixed positions with respect to each other. Points may be moved separately or in groups.

The materials of the point arrays and supports will vary as further research uncovers phenomena of interest arising from or responsive to differences in those materials.

Although the description above contains many specificities, these should not be construed as limiting the scope of the invention but as merely providing illustrations of some of the presently preferred embodiments of this invention. For example, the density, sharpness, type of electrical conductors or semiconductors connecting the points, constituent materials and arrangement of the points can assume all physically possible variations, and it is expected that, with further research, more novel and unexpected benefits will be discovered in other combinations of this basic combination of elements. Thus, the scope of the invention should be determined by the appended claims and their legal equivalents, rather than by the examples given.

What is claimed is:

1. A therapeutic device comprising:
   an array of members, including ferromagnetic members and diamagnetic members;
   at least one magnetic source magnetically coupled to said ferromagnetic members and said diamagnetic members, wherein magnetic coupling between said at least one magnetic source and said diamagnetic members is without dependency upon magnetic coupling between said at least one magnetic source and said ferromagnetic members, each said member thereby being connected to generate magnetic stimuli; and
   at least one source of electrical signals coupled to each of said ferromagnetic and diamagnetic members to generate electromagnetic stimuli, said at least one source of electrical signals including controls connected to enable variations of said electromagnetic stimuli by selectively adjusting applied said electrical signals to said ferromagnetic and diamagnetic members.

2. The therapeutic device of claim 1 wherein said at least one magnetic source includes a flexible permanent magnet with which each said ferromagnetic and diamagnetic member is in contact during application of said magnetic stimuli.

3. The therapeutic device of claim 1 wherein said members in said array are points exposed to contact skin of a person, said members being arranged within said array such that rows of said ferromagnetic members alternate with rows of said diamagnetic members.

4. The therapeutic device of claim 3 wherein said controls are connected to selectively enable and disable coupling of said electrical signals to said members on a row-by-row basis.

5. The therapeutic device of claim 3 wherein said array includes a plurality of first interconnections among subdivisions of said ferromagnetic members and includes a plurality of second interconnections among subdivisions of said diamagnetic members, said controls including switching connections which selectively control signal conductivity through each of said first interconnections and each of said second interconnections.

6. The therapeutic device of claim 1 further comprising monitoring means for determining effects of said magnetic and electromagnetic stimuli when applied to skin of a person.

7. The therapeutic device of claim 1 further comprising a power source connected to provide power to said at least one source of electrical signals, said power source being a component of a self-contained device that includes said array of members, said at least one magnetic source and said at least one source of electrical signals.

8. The therapeutic device of claim 1 wherein diamagnetic members include points formed of one of brass and copper, said ferromagnetic members including points formed of one of iron and steel.

9. A therapeutic device comprising:
   an array of points which are exposed to enable contact with a person's skin, said array of points being configured and dimensioned to restrict puncturing of said skin, each said point being metallic and being magnetically reactive;
   magnetic means located to expose each said point to a magnetic field such that magnetic exposure is generally equal among said points;
   signal means connected to apply electrical signals to each said point in said array; and
   field manipulation means connected to establish a time varying applied electromagnetic field at said person's skin, said field manipulation means including a plurality of switches in which different subdivisions of said points are controlled by different said switches with respect to alternative said electrical signals and with respect to enablement and disablement.

10. The therapeutic device of claim 9 wherein said points include ferromagnetic points and diamagnetic points.

11. The therapeutic device of claim 10 wherein said ferromagnetic points and diamagnetic points are arranged in alternating rows within said array, said switches being connected to enable switching on a row-by-row basis.

12. The therapeutic device of claim 9 further comprising a thermal module located to apply thermal stimuli at said person's skin simultaneously with application of said electromagnetic field.

13. The therapeutic device of claim 9 wherein said magnetic means is a permanent magnet which is flexible.

14. The therapeutic device of claim 9 further comprising access openings for sensors positioned to monitor effects at said person's skin during application of said electromagnetic field.

15. A therapeutic process comprising:
   providing an array of members in which each said member is both magnetically coupled to at least one magnetic source and electrically coupled to at least one electrical source of electrical signals, wherein each magnetic coupling to any one of said members is without dependency upon magnetic coupling to adjacent said members;
   selecting a plurality of instances of electromagnetic fields for application to a person's skin by combined operations of said magnetic and electrical sources, wherein said plurality of instances are determined to be therapeutically beneficial to said person; and
   operating said magnetic and electrical sources while said array of members is in contact with said person's skin such that said selected instances are implemented by variations over time.

16. The therapeutic process of claim 15 wherein providing said array includes utilizing first said members which are ferromagnetic and utilizing second said members which are diamagnetic, wherein operating said magnetic and electrical sources includes magnetically and electrically employing all of said first and second members to implement said plurality of instances.

* * * * *